(12) United States Patent
Khetani et al.

(10) Patent No.: US 7,459,560 B2
(45) Date of Patent: *Dec. 2, 2008

(54) PROCESSES AND INTERMEDIATES FOR RESOLVING PIPERIDYL ACETAMIDE STEREOISOMERS

(75) Inventors: Vikram Khetani, Jersey City, NJ (US); Yalin Luo, New Providence, NJ (US); Sowmianarayanan Ramaswamy, Bridgewater, NJ (US)

(73) Assignee: Celgene Corporation, Warren, NJ (US)

( * ) Notice: Subject to any disclaimer, the term of this patent is extended or adjusted under 35 U.S.C. 154(b) by 39 days.

This patent is subject to a terminal disclaimer.

(21) Appl. No.: 11/360,877

(22) Filed: Feb. 23, 2006

(65) Prior Publication Data

US 2006/0142583 A1 Jun. 29, 2006

Related U.S. Application Data

(63) Continuation of application No. 10/915,905, filed on Aug. 11, 2004, now abandoned, which is a continuation of application No. 09/283,645, filed on Apr. 1, 1999, now Pat. No. 6,962,997, which is a continuation of application No. 08/861,988, filed on May 22, 1997, now Pat. No. 5,936,091.

(51) Int. Cl.
*C07D 211/32* (2006.01)
(52) U.S. Cl. .................................... 546/233; 546/190
(58) Field of Classification Search ................. 546/229, 546/190, 233
See application file for complete search history.

(56) References Cited

U.S. PATENT DOCUMENTS

| | | | |
|---|---|---|---|
| 2,507,631 A | 5/1950 | Hartmann et al. ............ 260/294 |
| 2,838,519 A | 6/1958 | Rometsch et al. ........ 260/294.3 |
| 2,957,880 A | 10/1960 | Rometsch .................... 546/233 |
| 4,137,300 A | 1/1979 | Sheth et al. .................. 424/460 |
| 4,410,700 A | 10/1983 | Rice ............................ 546/149 |
| 4,794,001 A | 12/1988 | Mehta et al. ................. 424/458 |
| 4,882,166 A | 11/1989 | Graham et al. .............. 424/462 |
| 4,904,476 A | 2/1990 | Mehta et al. ................. 424/456 |
| 4,968,505 A | 11/1990 | Okada et al. ................. 424/400 |
| 4,986,987 A | 1/1991 | Ayer et al. ................... 424/473 |
| 4,992,445 A | 2/1991 | Lawter et al. ................ 514/279 |
| 5,104,899 A | 4/1992 | Young et al. ................. 514/646 |
| 5,114,946 A | 5/1992 | Lawter et al. ................ 514/279 |
| 5,133,974 A | 7/1992 | Paradissis et al. ........... 424/480 |
| 5,137,733 A | 8/1992 | Noda et al. .................. 424/497 |
| 5,156,850 A | 10/1992 | Wong et al. .................. 424/473 |
| 5,158,777 A | 10/1992 | Abramowitz et al. ....... 424/458 |
| 5,160,744 A | 11/1992 | Jao et al. ...................... 424/473 |
| 5,202,128 A | 4/1993 | Morella et al. ............... 424/469 |
| 5,217,718 A | 6/1993 | Colley et al. ................. 424/449 |
| 5,223,265 A | 6/1993 | Wong .......................... 424/473 |
| 5,229,131 A | 7/1993 | Amidon et al. .............. 424/451 |
| 5,232,705 A | 8/1993 | Wong et al. .................. 424/473 |
| 5,236,689 A | 8/1993 | Wong et al. .................. 424/473 |
| 5,283,193 A | 2/1994 | Yamamoto et al. .......... 435/280 |
| 5,284,769 A | 2/1994 | Evans et al. .................. 435/280 |
| 5,299,121 A | 3/1994 | Brill et al. ............... 364/413.01 |
| 5,308,348 A | 5/1994 | Balaban et al. .......... 604/892.1 |
| 5,326,570 A | 7/1994 | Rudnic et al. ............... 424/458 |
| 5,331,000 A | 7/1994 | Young et al. ................. 514/570 |
| 5,362,755 A | 11/1994 | Barberich et al. ........... 514/649 |
| 5,375,693 A | 12/1994 | Woosley et al. ............. 514/317 |
| 5,391,381 A | 2/1995 | Wong et al. .................. 424/473 |
| 5,425,950 A | 6/1995 | Dandiker et al. ............ 424/480 |
| 5,449,743 A | 9/1995 | Kobayashi et al. .......... 528/355 |
| 5,478,573 A | 12/1995 | Eichel et al. ................. 424/480 |
| 5,496,561 A | 3/1996 | Okada et al. ................. 424/480 |
| 5,500,227 A | 3/1996 | Oshlack et al. .............. 424/476 |
| 5,512,293 A | 4/1996 | Landrau et al. .............. 424/449 |
| 5,567,441 A | 10/1996 | Chen .......................... 424/494 |
| 5,580,578 A | 12/1996 | Oshlack et al. .............. 424/468 |
| 5,593,694 A | 1/1997 | Hayashida et al. .......... 124/468 |
| 5,639,476 A | 6/1997 | Oshlack et al. .............. 424/468 |
| 5,672,360 A | 9/1997 | Sackler et al. ............... 424/490 |
| 5,733,478 A | 3/1998 | Creech et al. ........... 252/400.21 |
| 5,733,756 A | 3/1998 | Zeitlin et al. ................. 435/122 |
| 5,837,284 A | 11/1998 | Mehta et al. ................. 424/459 |
| 5,874,090 A | 2/1999 | Baker et al. ................. 424/400 |
| 5,908,850 A | 6/1999 | Zeitlin et al. ................. 514/315 |
| 5,922,736 A | 7/1999 | Dariani et al. ............... 514/317 |
| 5,936,091 A * | 8/1999 | Khetani et al. .............. 546/233 |
| 5,965,734 A | 10/1999 | Ramaswamy et al. ....... 546/233 |
| 6,031,124 A | 2/2000 | Fox et al. ....................... 560/37 |
| 6,062,997 A | 5/2000 | Seymour ..................... 473/578 |
| 6,113,879 A | 9/2000 | Richards et al. ............. 424/9.1 |
| 6,121,453 A | 9/2000 | Zavareh ...................... 546/238 |
| 6,127,385 A | 10/2000 | Midha et al. ................. 514/317 |
| 6,217,904 B1 | 4/2001 | Midha et al. ................. 424/468 |
| 6,221,883 B1 | 4/2001 | Baldessarini ................ 514/317 |
| 6,228,398 B1 | 5/2001 | Devane et al. ............... 424/484 |

(Continued)

FOREIGN PATENT DOCUMENTS

CA   1 297 368   3/1992

(Continued)

OTHER PUBLICATIONS

Berrang, et al., "Enantiomeric aminopropiophenones," CA 97:38738, 1982.

(Continued)

*Primary Examiner*—Janet L. Andres
*Assistant Examiner*—David E Gallis
(74) *Attorney, Agent, or Firm*—Woodcock Washburn, LLP

(57) ABSTRACT

Processes and intermediates for preparing 2-substituted piperidines such as 2-substituted d-threo piperidines are provided, including processes and intermediates for resolution of piperidyl acetamide stereoisomers.

8 Claims, No Drawings

U.S. PATENT DOCUMENTS

| | | | |
|---|---|---|---|
| 6,242,464 B1 | 6/2001 | Harris et al. | 514/317 |
| 6,255,325 B1 | 7/2001 | Dariani et al. | 514/317 |
| 6,344,215 B1 | 2/2002 | Bettman et al. | 424/459 |
| 6,355,656 B1 | 3/2002 | Zeitlin et al. | 514/317 |
| 6,359,139 B1 | 3/2002 | Khetani et al. | 546/233 |
| 6,395,752 B1 | 5/2002 | Midha et al. | 514/317 |
| 6,441,178 B2 | 8/2002 | Zavareh et al. | 546/238 |
| 6,468,504 B1 | 10/2002 | Richards et al. | 424/9.1 |
| 6,486,177 B2 | 11/2002 | Zeldis et al. | 514/317 |
| 6,528,530 B2 | 3/2003 | Zeitlin et al. | 514/317 |
| 6,531,489 B2 | 3/2003 | Harris et al. | 514/317 |
| 6,602,887 B2 | 8/2003 | Dariani et al. | 514/317 |
| 6,635,284 B2 | 10/2003 | Mehta et al. | 424/497 |
| 6,730,325 B2 | 5/2004 | Devane et al. | 424/489 |
| 7,115,631 B2 | 10/2006 | Zeldis et al. | 514/317 |
| 2002/0019535 A1 | 2/2002 | Zavareh et al. | 546/227 |
| 2002/0032335 A1 | 3/2002 | Langston et al. | 546/238 |
| 2002/0103162 A1 | 8/2002 | Epstein et al. | 514/79 |
| 2002/0132793 A1 | 9/2002 | Epstein et al. | 514/79 |
| 2003/0049205 A1 | 3/2003 | Richards et al. | 424/9.1 |
| 2003/0105134 A1 | 6/2003 | Harris et al. | 514/317 |
| 2003/0170181 A1 | 9/2003 | Midha | 424/10.4 |

FOREIGN PATENT DOCUMENTS

| | | |
|---|---|---|
| CA | 2 368 367 A1 | 10/2000 |
| CA | 2 376 215 A1 | 12/2001 |
| CA | 2 223 643 C | 12/2003 |
| EP | 0 636 366 A2 | 2/1995 |
| EP | 0 885 191 B1 | 1/2002 |
| EP | 0 889 874 B1 | 1/2002 |
| EP | 0 841 928 B1 | 9/2002 |
| EP | 0 879 228 B1 | 10/2002 |
| EP | 0 958 281 B1 | 3/2004 |
| FR | 2 635 460 | 9/1994 |
| GB | 589625 | 1/1945 |
| GB | 788226 | 12/1957 |
| GB | 878167 | 9/1961 |
| SU | 466229 | 4/1975 |
| WO | 93/05769 A1 | 1/1993 |
| WO | 97/03671 A1 | 2/1997 |
| WO | 97/03672 A1 | 2/1997 |
| WO | 97/03673 A1 | 2/1997 |
| WO | 97/27176 A1 | 7/1997 |
| WO | 97/28124 A1 | 8/1997 |
| WO | 97/32851 A1 | 9/1997 |
| WO | 97/35836 A1 | 10/1997 |
| WO | 98/06380 A2 | 2/1998 |
| WO | 98/23263 A1 | 6/1998 |
| WO | 98/25902 A1 | 6/1998 |
| WO | 98/31668 A1 | 7/1998 |
| WO | 98/14168 A2 | 9/1998 |
| WO | 99/62496 A1 | 12/1999 |
| WO | 00/74680 A1 | 12/2000 |
| WO | 01/43730 A3 | 6/2001 |
| WO | 2004/026258 A2 | 4/2004 |

OTHER PUBLICATIONS

Branko, et al., "Determination of enantiomeric composition of 1-phenyl-2(2-piperidyl) acetamide," Tetrahedron: Asymmetry, 1994, 5, 1711-1716.

Brown, G., "The use of methylphenidate for cognitive decline associated with HIV disease," Int'l J. Psychiatry Med., 1995, 25(1), 21-37.

Dobashi, et al., "Enantioselectivity of hydrogen-bond," CA 106:66522, 1986.

Greenhill, "Attention Deficit Hyperactivity Disorder", Pediatric Psychopharmacology, 1995, 4(1), 123-168.

Japan Chem. Soc., "Organic reaction," 1958, 1(18), 504-505 (translation attached).

Patrick, et al., "Synthesis of deuterium labeled methylphenidate," J. Label. Pharm., 1982, 9, 484-490.

Vanderplas, B. et al., "A convenient synthesis of cis-1R-N-benzyl-2S-hydroxymethyl cyclohexylamine," CA 118:101538, 1992.

Aoyama, T., et al., "Nonlinear kinetics of threo-methylphenidate enantiomers in a patient with narcolepsy and in healthy volunteers," Eur. J. of Clinical Pharmacology, 1993, 44(1), 79-84.

Barkley, R. A., et al., "The adolescent outcome of hyperactive children diagnosed by research criteria: I. An 8-year prospective follow-up study," J. Am. Acad. Adolesc. Psychiatry., 1990, 29(4), 546-557.

Bruera, E., et al., "The uses of psychotropics in symptom management in advanced cancer," Psycho-Oncology., 1998, 7, 346-358.

CAS RN6051-31-6 or RN 3019-58-7.

Feng, et al., "Molecular determinants of the platelet," CA 117:111440, 1992.

Garland, E. J., "Pharmacotherapy of adolescent attention deficit hyperactivity disorder: challenges, choices and caveats," J. Psychopharmacology., 1998, 12(4), 385-395.

Golden, G. S., "Role of attention deficit hyperactivity disorder in learning disabilities," Seminars in Neurology., 1991, 11(1), 35-41.

Goldman, L. S., et al., "Diagnosis and treatment of attention-deficit/hyperactivity disorder in children and adolescents," J. Am. Med. Assn., 1998, 279(14), 1100-1107.

Jursic, et al., "Determination of enantiomeric composition of 1-phenyl-2(2-piperidinyl-acetamide)," Tetrahedron: asymmetry, 1994, 5, 1711-1716.

Morrison, et al., "Organic Chemistry," Allyn & Bacon, 1973, 32-34.

No author, "Methylphenidate hydrochloride," Environmental Health Perspectives, 1997, 105 (supp 1), 319.

Ohashi, N. et al., "Acyl(amino)naphthalene derivatives," CA 104:186157, 1985.

Spencer, T., et al., "Pharmacotherapy of attention-deficit hyperactivity disorder across the life cycle," J. Am. Acad. Adolesc. Psychiatry., 1996, 35(4), 409-432.

Srinivas et al., "Enantioselective pharmacokinetics and pharmacodynamics of racemic threo-methylphenidate in children with attention deficit hyperactivity disorder," Clin. Pharmacol. Ther., 1995, 52(2), 561-568.

Stein, M. A., et al., "Methylphenidate dosing: Twice daily versus three times daily," Pediatrics, 1996, 98(4), 748-756.

Swanson, J. M., et al., "Analog classroom assessment of Adderall in children with ADHD," J. Am. Acad. Adolesc. Psychiatry., 1998, 37(5), 519-525.

Ward, M. F., et al., "The Wender Utah rating scale: an aid in the retrospective diagnosis of childhood attention deficit hyperactivity disorder," Am. J. Psychiatry., 1993, 150(6), 885-890.

Zametkin, A. J. and Ernst, M., "Problems in the management of attention-deficit/hyperactivity disorder," New. Eng. Jour. Med., 1999, 340(1), 40-46.

Aoyama, T. et al., "Pharmacodynamic Modeling for Change of Locomotor Activity by Methylphenidate in Rats," Pharmaceutical Research, 1997, 14(11), 1601-1606.

Aoyama, T. et al., "Pharmacokinetics and pharmacodynamics of methylphenidate enantiomers in rats," Psychopharmacology, 1996, 127, 117-122.

Baughman, Jr., F. A., "Treatment of Attention-Deficit/Hyperactivity Disorder," JAMA., Apr. 28, 1999, 218(16), 1490-1491.

Carey, W. B., "What the multimodal treatment study of children with attention-deficit/hyperactivity disorder did and did not say about the use of methylphenidate for attention deficits," Pediatrics, 2000, 863-864.

Chapin, R., "Methylphenidate hydrochloride," Environ. Health Perspect., 1997, 105(1), 319-320.

Coyle, J. T., "Psychotic drug use in very young children," J. Am. Med. Assn., 2000, 283(8), 1059-1060.

Davids, E. et al., "Stereoselective effects of methylphenidate on motor hyperactivity in juvenile rats in neonatal 6-hydroxydopamine lesioning," Psychopharmacology, 2002, 160, 92-98.

Ding, Y.-S., "Chiral drugs: comparison of the pharmacokinetics of [11C]d-threo and l-threo-methylphenidate in the human and baboon brain," Psychopharmacology, 1997, 131, 71-78.

Ding, Y.-S. et al., "Is the L-threo Enantiomer of Methylphenidate (Ritalin) Inactive in the Brain when the Drug is Given Orally?" ACNP 41st Annual Meeting, Dec. 8-12, 2002, Scientific Abstract No. 119.

Jadad, A. R. et al., "Review: Pharmacologic interventions are more effective than non-pharmacologic for attention-deficit hyperactivity disorder," Therapeutics, ACP Journal Club., Nov./Dec. 2000, 110.

Jensen, P. S., et al., "Are stimulants over-prescribed? Treatment of ADHD in four U.S. communities," J. Am. Acad. Adolesc. Psychiatry., 1999, 37(7), 797-804.

Jonkman, L.M. et al., "Differences in plasma concentrations of the D- and L-threo methylphenidate enantiomers in responding and non-responding children with attention-deficit hyperactivity disorder," Psychiatry Research, 1998, 78, 115-118.

Kimko, H. C., et al., "Pharmacokinetics and Clinical effectiveness of methylphenidate," Clin. Pharmacokinetics., 1999, 37(6), 457-470.

LeFever, G. B., et al., "The extent of drug therapy for attention deficit-hyperactivity disorder among children in public schools," American Journal of Public Health, (Sep. 1999), (89)9, 1359-1364.

Llana, M. E. and Crismon, M. L., "Methylphenidate: increased abuse or appropriate use?," J. Amer. Pharmaceut. Assn., 1999, 39(4), 526-530.

Lin, J. H., and Lu, A. H., "Role of pharmacokinetics and Metabolism in drug discovery and development," Pharmacological Reviews, 1997, 49(4), 403-449.

MacDougall, M. K., et al., "Symptom control in the pregnant cancer patient," Seminars in Oncology., 2000, 27(6), 704-711.

Markowitz, J. S., et al., "Advances in the pharmacotherapy of attention-deficit-hyperactivity disorder: focus on methylphenidate formulations," Pharmacotherapy., 2003, 23(10), 1281-1299.

McCarthy, M., "USA to improve care of children with ADHD," The Lancet, 2000, 355, 1161.

Mehta, M. A., et al., "Methylphenidate enhances working memory by modulating discrete frontal and parietal lobe regions in the human brain," J. Neurosci., 2000, 20RC65, 1-6.

Modi, N. B. et al., "Dose-Proportional and Stereospecific Pharmacokinetics of Methylphenidate Delivered Using an Osmotic, Controlled-Release Oral Delivery System," J. Clin. Pharmacol., 2000, 40, 1141-1149.

Patrick K S et al: "The Absorption Of Sustained-Release Methylphenidate Formulations Compared To An Immediate-Release Formulation" Biopharmaceutics And Drug Disposition, Wiley, Chichester, US, vol. 10, No. 2, 1989, pp. 165-171.

Patrick, K.S. et al., "Pharmacology of Methylphenidate, Amphetamine Enantiomers and Pemoline in Attention-Deficit Hyperactivity Disorder," Human Psychopharmacology, 1997, 12, 527-546.

Patrick et al., "Pharmacology of the Enantiomers of threo-Methylphenidate", J. Pharmacol. Exp. Ther., 1987, 241, 152-158.

Quinn, D.M.P., "Methylphenidate: The Role of the d-Isomer," undated, Department of Psychiatry, College of Medicine, University of Saskatchewan, Saskatoon, Saskatchewan, Canada, 369-373.

Rice, K.C., et al., Organic Chem., 3rd Ed., 32-34.

Rouhi, A.M, "Chirality at Work," C&EN, May 5, 2003, 56-61.

Schweitzer J. B., et al., "Attention deficit hyperactivity disorder," Adv. Pathophysiol. And Treat. Psychiatric Disorders: Implications for Internal Med., 2001, 85(3), 757-777.

Shader R.I. et al., "Population Pharmacokinetics of Methylphenidate in Children with Attention-Deficit Hyperactivity Disorder," J Clin Pharmacol, 1999, 39, 775-785.

Srinivas, N.R. "Role of Stereoselective Asasys in Bioequivalence Studies of Racemic Drugs: Have We Reached a Consensus?" J. Clin. Pharmacol., 2004, 44, 115-119.

Srinivas, N.R., et al., "Enantiomeric Drug Development: Issues, Considerations, and Regulatory Requirements," Journal of Pharmaceutical Sciences, Sep. 2001, 90(9), 1205-1215.

Srinivas et al., "Enantiomeric Gas Chromatography Assay with Electron Capture Detection for d-Ritalinic Acid in Plasma", J. Chromatagraph., 1990, 530, 327-336.

Sun, Z. et al., "Methylphenidate is Stereoselectively Hydrolzyed by Human Carboxylesterase CES1A1," The Journal of Pharmacology and Experimental Therapeutics, 2004, 310(2), 469-476.

Swanson, J. M., et al., "Acute tolerance to methylphenidate in the treatment of attention deficit hyperactivity disorder in children," Clin. Pharmacology and Therapeut., 1999, 66(3), 295-305.

Taylor, M. A., "Attention-deficit hyperactivity disorder on the frontlines: Management in the primary care office," Comp. Ther., 1999, 25(6/7), 313-325.

Teo, S. K., et al., "A 90-day oral gavage toxicity study of D-methylphenidate and D,L-methylphenidate in beagle dogs," Internat. J. Toxicol., 2003, 22, 215-226.

Teo, S. K., et al., "A single-dose, two-way crossover, bioequivalence study of dexmethylphenidate HCl with and without food in healthy subjects," J. Clin. Pharmacol., Feb. 2004, 44, 173-178.

Teo, S. K., et al., "D-Methylphenidate and D,L-methylphenidate are not developmental toxicants in rats and rabbits," Birth Defects Research (Part B)., 2003, 68, 162-171.

Teo, S. K., et al., "D-Methylphenidate is non-genotoxic in in vitro and in vivo assays," Mutation Research., 2003, 537, 67-79.

Teo, S. K., et al., "Neurobehavioral effects of racemic threo-methylphenidate and its D and L enantiomers in rats," Pharmacology, Biochemistry, and Behavior, 2003, 74, 747-754.

Teo, S., et al., "A 90-day oral gavage toxicity study of D-methylphenidate and D,L-methylphenidate in Sprague-Dawley rats," Toxicology, 2002, 179, 183-196.

Teo, S.K. et al., "The perinatal and postnatal toxicity of D-methylphenidate and D,L-methylphenidate in rats," Reproductive Toxicology, 2002, 16, 353-366.

Thai, D.L., et al., "Comparative Pharmacokinetics and Tissue Distribution of the d-enantiomers of Para-substituted Methylphenidate Analogs," Drug Metabolism and Disposition, 1999, 27(6), 645-650.

Thomson, M.R., et al., "Enantioselective Transesterification of Methylphenidate to Ethylphenidate After Coadministration with Ethanol," Thirty-First Annual ACCP Meeting Abstracts, Abstract No. 80, 2002, 1 page.

Tripp, G. and Alsop, B., "Sensitivity to reward frequency in boys with attention deficit hyperactivity disorder," J. Clin. Child Psychology., 1999, 28(3), 366-375.

Volkow, N. D. et al., "Mechanism of action of methylphenidate: Insights from PET imaging studies," Journal of Attention Disorders, 2002, 9(Suppl. Jan. 2002), S31-S43.

Volkow, N.D. et al., "Effects of Methylphenidate on Regional Brain Glucose Metabolism in Humans: Relationship to Dopamine $D_2$ Receptors," Am J Psychiatry, Jan. 1997, 154(1), 50-55.

Volkow, N.D. et al., "Evidence That Methylphenidate Enhances the Saliency of a Mathematical Task by Increasing Dopamine in the Human Brain," Am J Psychiatry, Jul. 2004, 161(7), 1173-1180.

Volkow, N.D. et al., "Temporal relationships between the pharmacokinetics of methylphenidate in the human brain and its behavioral and cardiovascular effects," Psychopharmacology, 1996, 123, 26-33.

Weiler, M. D., et al., "Mother and Teacher Reports of ADHD Symptoms: DSM-IV Questionnaire Data," J. Am. Acad.Child Adolesc. Psychiatry, Sep. 1999, 38(9), 1139-1147.

Zito, J. M., et al., "Trends in the prescribing of psychotropic medications to preschoolers," J. Am. Med. Assn., 2000, 283(8), 1025-1030.

Angrist, B., et al., "Central nervous system stimulants as symptomatic treatments for AIDS-related neuropsychiatric impairment," J. Clin. Psychopharm., 1992, 12(4), 268-272.

Aoyama et al., "Pharmacokinetics and pharmacodynamics of (+)-threo-methylphenidate enantiomer in patients with hypersomnia", Clin. Pharmacol. Ther., 1994, 55(3), 270-276.

Aoyama, T., et al., "Kinetic analysis of enantiomers of threo-methylphenidate and its metabolite in two healthy subjects after oral administration as determined by a gas chromatographic-mass spectrometric method," J. of Pharm. Sciences, 1990, 79(6), 465-569.

Aoyama, T., et al., Gas chromatographic-mass spectrometric analysis of threo-methylphenidate enantiomers in plasma, J. Chromatography, 1989, 494, 420-423.

Avis, K.E., "Parenteral Preparations," *Remington's Pharmaceutical Sciences*, 16th Ed., Osol, A. (Ed.), Mack Publishing Co., 1980, 1463-1487.

Axten, J.M., et al., "A stereoselective synthesis of dl-threo-methylphenidate: preparation and biological evaluation of novel analogues," J. Org. Chem., 1998, 63, 9628-9629.

Axten, J.M., et al., "Enantioselective synthesis of D-threo-methylphenidate," J. Am. Chem. Soc., 1999, 121, 6511-6512.

Barkley et al., "Side effects of methylphenidate in children with attention deficit hyperactivity disorder: A systemic, placebo-controlled evaluation," Pediatrics, 1990, 86(2), 184-192.

Barkley et al., "Attention deficit disorder with and without hyperactivity: clinical response to three dose levels of methylphenidate," Pediatrics, 1991, 87(4), 519-531 (Abstract only).

Bowden, K., "Reactions of carbonyl compounds in basic solutions, Part 15. The alkaline hydrolysis of N-methyl, N-phenyl, and bicyclo lactams, penicillins, and N-alkyl-N-methylacetamides," J. Chem. Soc. Perkin Trans. 2, 1990, 2111-2116.

Bruera, E., et al., "Methylphenidate associated with narcotics for the treatment of cancer pain," Cancer Treat. Rep., 1987, 71(1), 67-70.

Bruera, E., et al., "Neuropsychological effects of methylphenidate in patients receiving a continuous infusion of narcotics for cancer pain," Pain, 1992, 48, 163-166.

Challman, T.D., et al., "Methylphenidate: Its pharmacology and uses," Mayo Clin. Proc., 2000, 75, 711-721.

Corey et al., "A New Synthetic Approach to the Penicillins", J. Am. Chem. Soc., 1965, 87(11), 2518-2519.

Davies, H.M.L., et al., "Highly regio-, diastereo-, and enantioselective C—H insertions of methyl aryldiazoacetates into cyclic N-boc-protected amines, asymmetric synthesis of novel $C_2$-symmetric amines and threo-methylphenidate," J. Am. Chem. Soc., 1999, 121, 6509-6510.

Deutsch, H.M., et al., "Synthesis and pharmacology of potential cocaine antagonists. 2. Structure-activity relationship studies of aromatic ring-substituted methylphenidate analogs," J. Med. Chem., 1996, 39, 1201-1209.

Ding et al., Cis- and trans-Azetidin-2-ones from Nitrones and Copper Acetylide, J.C.S. Perkin I., 1976, 2382-2386.

Ding, Y-S. et al., "Brain Kinetics of Methylphenidate (Ritalin) Enantiomers After Oral Administration," Synapse, 2004, 53, 168-175.

Dirksen, S.J.H., et al., "A postmarketing clinical experience study of Metadate® CD," Current Med. Res. And Opinion, 2002, 18(7), 371-380.

Douzenis et al., "Psychiatric Disorder in HIV Disease: Description of 200 Referrals to a Liaison psychiatry Service", Proc. 7th. Int'l Conf. AIDS, 1991, 215 (M.B.2135—Summary).

Drimmer, E.J., et al., "Desipramine and methylphenidate combination treatment for depression: case report," Am. J. of Psychiatry, 1983, 140(2), 241-242.

Earle et al., "Synthesis and Hydrolysis of some Fused-ring β-Lactarns", J. Chem. Soc. (C), 1969, 2093-2098.

Eckerman, D.A., et al., "Enantioselective behavioral effects of threo-methylphenidate in rats," Pharmacology Biochem. & Behav., 1991, 40, 875-880.

Fernandez, F., et al., "Methylphenidate for depressive disorders in cancer patients," Psychosomatics, 1987, 28(9), 455-461.

Ferris, R.M., et al., "A comparison of the capacities of isomers of amphetamine, deoxypipradol and methylphenidate to inhibit the uptake of tritiated catecholamines into rat cerebral cortex slices, synaptosomal preparations of rat cerebral cortex, hypothalamus and striatum and into adrenergic nerves of rabbit aorta," J. of Pharmacology & Experimental Therapeutics, 1972, 181(3), 407-416.

Ferris, R.M., et al., "Comparison of the effects of the isomers of amphetamine, methylphenidate and deoxypipradol on the uptake of 1-[$^3$H]norepinephrine and [$^3$H]dopamine by synaptic vesicles from rat whole brain, striatum and hypothalamus," J. of Pharmacology & Experimental Therapeutics, 1979, 210(3), 422-428.

Golinko, B. E., "Side effects of dextroamphetamine and methylphenidate in hyperactive children—a brief review," Prog. Neuro-Psychopharmacol. & Biol. Psychiat., 1984, 8(1), 1-8.

Grob, C.S., et al., "Suspected adverse methylphenidate-imipramine interactions in children," J. of Develop. & Behav. Pediatrics, 1986, 7(4), 265-267.

Holmes et al., "Psychostimulant response in AIDS-related complex patients," J. Clin. Psychiatry, 1989, 50(1), 5-8, Biosis Abstract No. 87129969.

Hou, J.P. et al., "β-Lactam Antibiotics: Their Physiochemical Properties and Biological Activities in Relation to Structure", J. Pharm. Sci., 1971, 60(4), 503-532.

Hubbard, J.W., et al., "Enantioselective aspects of the disposition of dl-threo-methylphenidate after the administration of a sustained-release formulation to children with attention deficit-hyperactivity disorder," J. of Pharmaceutical Sciences, 1989, 78(11), 944-947.

Hyneck, M., et al., "Chirality: Pharmacological Action and Drug Development," *Chirality In Drug Design And Synthesis*, Brown, C. (Ed.), Academic Press, London, 1990, 4-7.

Kadouch, et al., Neuropsychobiology, 1977, 3(4), 250-255, HCAPLUS Abstract 88:115433.

Klibanov, A.M., "Asymmetric Transformation Catalyzed by Enzymes in Organic Solvents", Acc. Chem. Res., 1990, 23, 114-120.

Licamele, W.L., et al., "The concurrent use of lithium and methylphenidate in a child," J. of the Am. Acad. Of Child Adolescent Psychiatry, 1989, 28(5), 785-787.

Lim, H.K. et al., "Enantiomeric resolution of dl-threo-methylphenidate, U.S.P. (Ritain®), by high-performance liquid chromatography," J. of Chromatography, 1985, 328, 378-386.

Macleod, A.D., "Methylphenidate in terminal depression," J. of Pain & Symptom Management, 1998, 16(3), 193-198.

Matsumura, Y., et al., "A convenient method for synthesis of enantiomerically enriched methylphenidate from N-methoxycarbonylpiperidine," Organic Letters, 1999, 1(2), 175-178.

Meyers, C.A., et al., "Methylphenidate therapy improves cognition, mood, and function of brain tumor patients," J. of Clinical Oncology, 1998, 16(7), 2522-2527.

Moll F., "Darstellung von 1-Aza-bicyclo[4.2.0]octan-2-on", Z. Naturforschg, 1966, 21b, 297.

Naito, T., et al., "Rearrangement of sulfonamide derivatives. V. Syntheses of methyl α-phenyl-2- and 4-piperidineacetate," Chem. Pharm. Bull., 1964, 12(5), 588-590.

Navia et al., "The AIDS Dementia Complex: I. Clinical Features", Annals of Neurology, 1986, 19(6), 517-524.

Panizzon, Leandro, "Preparation of pyridyl- and piperidylarylacetonitriles and of a number of conversion products (Part I).", Helvetica Chimica Acta, 1944, 27, 1748-1756.

Patrick, K. S. et al., "New methylphenidate formulations for the treatment of attention-deficit/hyperactivity disorder," Expert Opin. Drug Deliv., 2005, 2(1), 121-143.

Patrick, K.S. et al., "Synthesis, Pharmacology and Human Metabolic Formation of Ethylphenidate: the Transesterification Product of Methylphenidate and Ethanol," The 56th Southeast Regional Meeting 2004, Nov. 10-13, 2004, 1 page.

Physician's Desk Reference, 46th Ed., 1992, 880-881.

Prashad, M., et al., "Enzymatic resolution of (±)-threo-methylphenidate," Tetrahedron: Asymmetry, 1998, 9, 2133-2136.

Prashad, M., et al., "Enantioselective synthesis of (2S,2'R)-erythro-methylphenidate," Tetrahedron: Asymmetry, 1999, 10, 3479-3482.

Prashad, M., "The first enantioselective synthesis of (2R,2',R)-threo(+)-methylphenidate hydrochloride," J. Org. Chem., 1999, 64, 1750-1753.

Quinn, D., et al., "Comparative pharmacodynamics and plasma concentrations of d-threo-methylphenidate hydrochloride after single doses of d-threo-methylphenidate hydrochloride and d,1-threo-methylphenidate hydrochloride in a double-blind, placebo-controlled, crossover laboratory school study in children with attention-deficit/hyperactivity disorder," J. Am. Acad. Child Adolesc. Psychiatry, 2004, 43(11), 1422-1429.

Rapport, M.D., et al., "Methylphenidate and desipramine in hospitalized children: I. Separate and combined effects on cognitive function," J. of the Am. Acad. Of Child Adolescent Psychiatry, 1993, 32(2), 333-342.

Rieder et al., "Diagnosis of Sulfonamide Hypersensitivity Reactions by In-Vitro "Rechallenge" with Hydroxylamine Metabolites", Ann. Intern Med., 1989, 110(4), 286-289.
Rochdi, M., et al., "Dose-proportional pharmacokinetics of a methylphenidate extended-release capsule," Int. J. of Clin. Pharma. And Theraps., 2004, 42(5), 285-292.
Roehrs, T., et al., "Sleepiness and the reinforcing and subjective effects of methylphenidate," Exp. Clin. Psychopharmacol., 1999, 7(2), 145-150 (Abstract only).
Sarhill, N., et al., "Methylphenidate for fatigue in advanced cancer: a prospective open-label pilot study," Am. J. of Hospice & Palliative Care, 2001, 18(3), 187-192.
Scott, "Stereoisomers and Drug Toxicity; The value of single stereoisomer therapy", Drug Safety Concepts, 1993, 8(2), 149-159.
Srinivas et al., "Enantioselective Pharmacokinetics of dl-threo-Methylphenidate in Humans", Pharmaceutical Research, 1993, 10(1), 14-21.
Srinivas et al., "Stereoselective Disposition of Methylphenidate in Children with Attention Deficit Disorder", J. Pharmacol. Exp. Ther., 1987, 241(1), 300-306.
Srinivas, N.R., et al., "In vitro hydrolysis of RR,SS-threo-methylphenidate by blood esterases-differential and enantioselective interspecies variability," Chirality, 1991, 3, 99-103.
Staal et al., "Glutathione deficiency and human immunodeficiency virus infection", Lancet, 1992, 339, 909-912.
Stiebel, V., et al., "Long-term methylphenidate use in the medically ill patient with organic mood syndrome," Psychosomatics, 1990, 31(4), 454-456.
Thai, D.I., et al., "Asymmetric synthesis and pharmacology of methylphenidate and its para-substituted derivatives," J. Med. Chem., 1998, 41, 591-601.
Tyndale, R.F., et al., "Neuronal cytochrome P450IIDI (Debrisoquine/sparteine-type): potential inhibition of activity by (-)-cocaine and nucleotide sequence identity to human hepatic P450 gene CYP2D6," Molecular Pharmacology, 1991, 40, 63-68.
Uetrecht, J.P. et al., "Idiosyncratic Drug Reactions: Possible Role of Reactive Metabolites Generated by Leukocytes", Pharmaceutical Res., 1989, 6(4), 265-273.
Weiss, M., et al., "A post hoc analysis of d-threo-methylphenidate hydrochloride (Focalin) versus d,l-threo-methylphendiate hydrochloride (Ritalin)," J. Am. Acad. Child Adolesc. Psychiatry, 2004, 43(11), 1415-1421.
Weitzner, M.A., et al., "Methylphenidate in the treatment of neurobehavioral slowing associated with cancer and cancer treatment," J. of Neuropsychiatry, 1995, 7(3), 347-350.
White et al., "Methylphenidate as a Treatment for Depression in Acquired Immunodeficiency Syndrome: An n-of-1 Trial", J. Clin. Psychiatry, 1992, 53(5), 153-156.
Wigal, S., et al., "A double-blind, placebo-controlled trial of dexmethylphenidate hydrochloride and d,l-threo-methylphenidate hydrochloride in children with attention-deficit/hyperactivity disorder," J. Am. Acad. Child Psychiatry, 2004, 43(11), 1406-1414.
"Attention-deficit and disruptive behavior disorders: Attention-deficit/hyperactivity disorder," American Psychiatric Association, Diagnostic and Statistical Manual of Mental Disorders, Fourth Ed. (DSM-IV) Washington, DC, 1994, 78-85.
Al Abwal, H. et al., "The effects of methylphenidate (MP) on narcotic-induced cognitive failure (MICF)," Am. Soc. Clin. Oncology, 27th Annual Meeting, May 19-21, 1991, 1385, 1992, vol. 11, p. 397.
Arnold, L. E. et al., "A Double-Blind, Placebo-Controlled Withdrawal Trial of Dexmethylphenidate Hydrochloride in Children with Attention Deficit Hyperactivity Disorder," 2004, J. Am. Child Adolesc. Psychopharmacol. 14(4):542-554.
Beck, A.T., et al., "Assessment of depression: the depression inventory," Mod. Probl. Pharmacopsychiatry, 1974, 7, 155-169.
Berrang, B. et al., "Enantiomeric alpha aminopropiophenones (cathinone): preparation and investigation," J. Org Chem., 1982, 47(13), 2643-2647.
Brown, T.E., "Emerging understandings of attention-deficit disorders and comorbidities," Attention-Deficit Disorders and Comorbidities in Children, Adolescents, and Adults, American Psychiatric Press, Inc., 2000, Washinton, DC, Chapter 1, 3-55.

Bruera, E., et al., "Narcotics plus methylphenidate (ritalin) for advanced cancer pain," Am. J. Nursing, Pain and Symptom Consult, Nov. 1988, 1665-1666.
Bruera, E., et al., "Overwhelming fatigue in advanced cancer," Am. J. Nursing, Pain Consult, Jan. 1988, 99-100.
Bruera, E., et al., "The use of methylphenidate in patients with incident cancer pain receiving regular opiates, A preliminary report," Pain, ISSN 0304-3959, Jul. 1992, 50(1), 75-77.
Bruera, E., et al., "Use of methylphenidate as an adjuvant to narcotic analgesics in patients with advanced cancer," J. Pain and Symptom Management, Mar. 1989, 4(1), 3-6.
Cella, D.F., et al., "The functional assessment of cancer therapy scale: development and validation of the general measure," J. Clin. Oncol., 1993, 11(3), 570-579.
DeLong, R., et al., "Methylphenidate in neuropsychological sequelae of radiotherapy and chemotherapy of childhood brain tumors and leukemia," J. Child Neurology, Oct. 1992, 7, 462-463.
Faust, D., et al., "The development and initial validation of a sensitive bedside cognitive screening test," J. Nerv. Ment. Dis., 1989, 177(1), 25-31.
Folstein, S.E., et al., "Minimental state : a practical method for grading the cognitive state of patients for the clinician," J. Psychiatry Res., 1975, 12, 189-198.
Greenhill, "Pharmacologic Treatment of Attention Deficit Hyperactivity Disorder", Pediatric Psychopharmacology, 1992, 15(1), 1-27.
Hales, R.E., et al., "Psychopharmacologic issues in the diagnosis and treatment of organic mental disorders," Psychia. Clinics of North America, Dec. 1984, 7(4), 817-829.
Jaffe, P., "Will the real Ritalin please stand up?," ADDendum—A Quarterly Newsletter by ad for Adults who have Attention Deficit Disorder, 1992, Issue #10, 3 pages.
Jarvi et al., "Bioequivalence of Methylphenidate Tablets," Abstract PPDM 8169, Pharmaceutical Research vol. 7, No. 9, 1990, 2 pages.
Massie, M. J. et al., "Diagnosis and treatment of depression in the cancer patient," Clinical Psychiatry, Mar. 1984, vol. 45, 3(2), 25-29.
Meyer, et al., "Bioequivalence of Methylphenidate Immediate-Release Tablets Using a Replicated Study Design to Characterize Intrasubject Variability," Pharmaceutical Research, vol. 17, No. 4, 2000, 381-384.
Nakano, T. et al., Algorithm for the treatment of major depression in patients with advanced cancer, Psychiatry and Clinical Neurosciences, Proceedings of the International Meeting on Japanese Psychopharmacology Algorithms, Yokohama, Apr. 23, 1998, ISSN1323-1316, 1999, Supplement 53, S61-S65.
O'Neill, W. M., "The cognitive and psychomotor effects of opioid drugs in cancer pain management," Cancer Surveys, Palliative Medicine Problem Areas in Pain and Symptom Management, 1994, 21, 67-84.
Olin, J. et al., "Psychostimulants for depression in hospitalized cancer patients," Psychosomatics, Jan.-Feb. 1996, 37(1), 57-62.
Patrick et al., "Distribution of Methylphenidate and P-Hydroxymethylphenidate in Rats," Journal of Pharmacology and Experimental Therapeutics, 1984, vol. 231, No. 1, 61-65.
Pelham, W. E. et al., "Sustained Release and Standard Methylphenidate Effects on Cognitive and Social Behavior in Children with Attention Deficit Disorder," Pediatrics, Oct. 1987, 80(4), 491-501.
Plutchik, L., et al., "Methylphenidate in post liver transplant patients," Psychosomatics, Mar.-Apr. 1998, 39(2), 119-123.
Radloff, L.S., "The CES-D scale: a self-report depression scale for research in the general population," Applied Psychological Measurement, Summer 1977, 1(3), 385-401.
Reich, M.G., "Amphetamines in oncology: review of the literature," Cancer, 1996, 83, 891-900 (English abstract).
Reitan, R.M., "Validity of the trail making test as an indicator of organic brain damage," Perceptual Motor Skills, 1958, 8, 271-276.
Silva, R. et al., "Open-Label Study of Dexmethylphenidate Hydrochloride in Children and Adolescents with Attention Deficit Hyperactivity Disorder," 2004, J. Child Adolesc. Psychopharmacol. 14(4):555-563.
Soares, J. R., "Stereochemical studies on potential central nervous system active agents and studies on the chemistry of some 3-benzoylpiperidines," UMI Disssertation Services, 1971, 1-180.

Srinivas, N. R., Thesis entitled "Enantioselective Pharmacokinetics of dl-threo-Methylphenidate in Children with Attention Hyperactivity Disorder and Healthy Adults," Thesis submission date: Apr. 1991.

Vigano, A. et al., "Methylphenidate for the management of somatization in terminal cancer patients," *J Pain and Symptom Management*, Feb. 1995, 10(2), 167-170.

Weitzner, M. A. et al., "The functional assessment of cancer therapy (FACT) scale: development of a brain subscale and revalidation of the general version (FACT-G) in patients with primary brain tumors," *Cancer*, Mar. 1, 1995, 75(5), 1151-1161.

Wilens, T. E. et al., "Pharmacotherapy of attention-deficit/hyperactivity disorder," *Attention-Deficit Disorders with Comorbidities*, Ch. 16, 509-535 (1995).

Wilwerding, M. B. et al., "A randomized crossover evaluation of methylphenidate in cancer patients receiving strong narcotics," *Soc. Clin. Oncology*, 29th Annual Meeting, May 16-18, 1993, 1615, 1993, vol. 12, p. 464.

Yee, J. D. et al., "Dextroamphetamine or methylphenidate as adjuvants to opioid analgesia for adolescents with cancer," *J Pain and Symptom Management*, Feb. 1994, 9(2), 122-125.

Yellen, S.B., et al., "Measuring fatigue and other anemia-related symptoms with the functional assessment of cancer therapy (FACT) measurement system," *J. pain Symptom Manage.*, Feb. 1997, 13(2), 63-74.

In the United States District Court For The District of New Jersey, Civil Action No. 04-CV-04030 (FLW), *Celgene Corporation, Novartis Pharmaceuticals Corporation and Novartis Pharma A.G.* v. *Teva Pharmaceuticals USA, Inc.*: Complaint for Patent Infringement with attached Exhibits A,B and C (Dec. 21, 2006).

In the United States District Court For The District of New Jersey, Civil Action No. 04-CV-04030 (FLW) and Civil Action No. 06-CV-6154 (FLW), *Celgene Corporation, Novartis Pharmaceuticals Corporation and Novartis Pharma A.G.* v. *Teva Pharmaceuticals USA, Inc.*: First Amended Answer and Counterclaim of Defendant Teva Pharmaceuticals USA, Inc. in Civil Action No. 06-CV-6154 (FLW) (Mar. 23, 2007).

In the United States District Court For The District of New Jersey, Civil Action No. 04-cv-04030 (FLW) and Civil Action No. 06-CV-6154 (FLW), *Celgene Corporation, Novartis Pharmaceuticals Corporation and Novartis Pharma A.G.* v. *Teva Pharmaceuticals USA, Inc.*: Plaintiff's Reply to Defendent's First Amended Counterclaim in Civil Action No. 06-CV-6154 (FLW) (Apr. 12, 2007).

In the United States District Court For The District of New Jersey, Civil Action No. 06-CV-05818 (SDW), *Celgene Corporation, Novartis Pharmaceuticals Corporation and Novartis Pharma A.G.* v. *Abrika Pharmaceuticals, Inc. and Abrika Pharmaceuticals, LLLP*: Complaint For Patent Infringement with attached Exhibits A and B (Dec. 4, 2006).

In the United States District Court For The District of New Jersey, Civil Action No. 2:06-CV-05818 (SDW)(MCA), *Celgene Corporation, Novartis Pharmaceuticals Corporation and Novartis Pharma A.G.* v. *Abrika Pharmaceuticals, Inc. and Abrika Pharmaceuticals, LLLP*, Answer and Counterclaim (Jun. 1, 2007).

In the United States District Court For The District of New Jersey, Civil Action No. 06-CV-05818 (SDW), *Celgene Corporation, Novartis Pharmaceuticals Corporation and Novartis Pharma A.G.* v. *Abrika Pharmaceuticals, Inc. and Abrika Pharmaceuticals, Inc. and Abrika Pharmaceuticals, LLLP*: Plaintiff's Reply to the Counterclaim (Jun. 25, 2007).

In the United States District Court For The District of New Jersey, Civil Action No. 07-CV-04459 (FLW)(JJH), *Celgene Corporation, Novartis Pharmaceuticals Corporation and Novartis Pharma A.G.* v. *Teva Pharmaceuticals USA, Inc.*: Complaint for Patent Infringement with attached Exhibits A-E (Sep. 14, 2007).

In the United States District Court For The District of New Jersey, Civil Action No. 2:06-CV-05818, *Celgene Corporation, Novartis Pharmaceuticals Corporation and Novartis Pharma A.G.* v. *Abrika Pharmaceuticals, Inc. and Abrika Pharmaceuticals, LLLP*: Defendant's First Supplemental Response to Plaintiff Celgene Corporation's Interrogatories Nos. 6-10 (Sep. 28, 2007).

In the United States District Court For The District of New Jersey, Civil Action No. 2:07-cv-04819-SDW-MCA, *Celgene Corporation, Novartis Pharmaceuticals Corporation and Novartis Pharma A.G.* v. *KV Pharmaceutical Company*: Complaint for Patent Infringement with attached Exhibits A and B (Oct. 4, 2007).

In the United States District Court For The District of New Jersey, Civil Action No. 3:07-cv-04854-FLW-JJH, *Celgene Corporation, Novartis Pharmaceuticals Corporation and Novartis Pharma A.G.* v. *Intellipharmaceutics Corp.*: Complaint For Patent Infringement with attached Exhibits A-E (Oct. 5, 2007).

In the United States District Court For The District of New Jersey, *Celgene Corporation, Novartis Pharmaceuticals Corporation and Novartis Pharma A.G.* v. *Barr Laboratories, Inc. and Barr Pharmaceuticals, Inc.*: Complaint For Patent Infringement with attached Exhibits A and B (Oct. 31, 2007).

In the United States District Court For The District of New Jersey, Civil Action No. 04-CV-4030 (SRC), *Celgene Corporation, Novartis Pharmaceuticals Corporation and Novartis Pharma A.G.* v. *Teva Pharmaceuticals USA, Inc.*: Defendant Teva Pharmaceuticals USA, Inc.'s Supplemental Responses to Plaintiff Celgene Corporation's First Set of Interrogatory Nos. 1-2, 4-7 and 10-15 (Jul. 14, 2005.

In the United States District Court For The District of New Jersey, Civil Action No. 04-CV-4030 (SRC), *Celgene Corporation, Novartis Pharmaceuticals Corporation and Novartis Pharma A.G.* v. *Teva Pharmaceuticals USA, Inc.*: Defendant Teva Pharmaceuticals USA, Inc.'s Second Supplemental Responses to Plaintiff Celgene Corporation's First Set of Interrogatory Nos. 1, 5, 10-11, and 14 (Aug. 19, 2005).

Amended Answer and Counterclaims of Defendant Teva Pharmaceuticals USA, Inc., filed Nov. 9, 2005, Civil Action No. 04-4030(SRC), *Celgene Corporation, Novartis Pharmaceuticals Corporation and Novartis Pharma AG* v. *Teva Pharmaceuticals USA, Inc.* Subject to Protective Order.

Study 97-M-01, Clinical Study Report, Mar. 10, 1998, Comparative Pharmacokinetics, Pharmacodynamics, and Safety of Single Doses of d-threo-Methylphenidate Hydrochloride and dl-threo-Methylphenidate Hydrochloride in Children With Attention Deficit/Hyperactivity Disorder. Subject to Protective Order.

Complaint, filed Aug. 19, 2004, Civil Action No. 04-4030(SRC), *Celgene Corporation, Novartis Pharmaceuticals Corporation and Novartis Pharma AG* v. *Teva Pharmaceuticals USA, Inc.*.

Answer and Counterclaim of Defendant Teva Pharmaceuticals USA, Inc., filed Nov. 9, 2004, Civil Action No. 04-4030(SRC), *Celgene Corporation, Novartis Pharmaceuticals Corporation and Novartis Pharma AG* v. *Teva Pharmaceuticals USA, Inc.*.

Plaintiffs' Reply to Defendant's Counterclaim, filed Nov. 29, 2004, Civil Action No. 04-4030(SRC), *Celgene Corporation, Novartis Pharmaceuticals Corporation and Novartis Pharma AG* v. *Teva Pharmaceuticals USA, Inc.*.

Redacted Amended Answer and Counterclaims of Defendant Teva Pharmaceuticals USA, Inc., filed Nov. 9, 2005, Civil Action No. 04-4030(SRC), *Celgene Corporation, Novartis Pharmaceuticals Corporation and Novartis Pharma AG* v. *Teva Pharmaceuticals USA, Inc.*.

Plaintiffs' Reply to Defendant's Amended Counterclaims, filed Dec. 5, 2005, Civil Action No. 04-4030(SRC), *Celgene Corporation, Novartis Pharmaceuticals Corporation and Novartis Pharma AG* v. *Teva Pharmaceuticals USA, Inc.*.

Confidential, Trade Secret, and/or Proprietary Document, dated Jul. 8, 2004.

Confidential, Trade Secret, and/or Proprietary Document, dated Jul. 27, 2004.

Confidential, Trade Secret, and/or Proprietary Document, dated Oct. 23, 2006.

Confidential, Trade Secret, and/or Proprietary Document, dated Aug. 3, 2007.

Confidential, Trade Secret, and/or Proprietary Document, dated Aug. 21, 2007.

Confidential, Trade Secret, and/or Proprietary Document, dated Aug. 23, 2007.

Confidential, Trade Secret, and/or Proprietary Document, dated Sep. 17, 2007.

Confidential, Trade Secret, and/or Proprietary Document, dated Sep. 26, 2007.

Confidential, Trade Secret, and/or Proprietary Document, dated Sep. 26, 2007.

Confidential, Trade Secret, and/or Proprietary Document, dated Oct. 5, 2007.

In the United States Patent and Trademark Office, File History of *Ex Parte* Reexamination of Patent No. 6,355,656, Control NO. 90/007,177, Reexamination Certificate Issued on Mar. 27, 2007.

In the United District Court For The District of New Jersey, Civil Action No. 07-CV-4459 (FLW), *Celgene Corporation, Novartis Pharmaceuticals Corporation and Novartis Pharma A.G. v. Teva Pharmaceuuticals USA, Inc.*: Teva's Answer and Counterclaims, Nov. 5, 2007.

In the United District Court For The District of New Jersey, Civil Action No. 07-CV-4459 (FLW), *Celgene Corporation, Novartis Pharmaceuticals Corporation and Novartis Pharma A.G. v. Teva Pharmaceuuticals USA, Inc.*: Plaintiff's Reply to Defendant's Counterclaims, Nov. 28, 2007.

In the United District Court For The District of New Jersey, Civil Action No. 07-CV-4854 (FLW) (JJH), *Celgene Corporation, Novartis Pharmaceuticals Corporation and Novartis Pharma A.G. v. Intellipharmaceuticals Corp.*: Answer and Counterclaims Demand For Jury Trial, Nov. 20, 2007.

In the United District Court For The District of New Jersey, Civil Action No. 07-CV-4854 (FLW) (JJH), *Celgene Corporation, Novartis Pharmaceuticals Corporation and Novartis Pharma A.G. v. Intellipharmaceuticals Corp.*: Plaintiff's Reply to Defendant's Counterclaims, Dec. 28, 2007.

In the United District Court For The District of New Jersey, Civil Action No. 07-CV-5367 (FLW) (TJB), *Celgene Corporation, Novartis Pharmaceuticals Corporation and Novartis Pharma A.G. v. Actavis South Atlantic LLC and Abrika Pharmaceuticals, Inc.*: Complaint for Patent Infringement, Nov. 8, 2007.

In the United District Court For The District of New Jersey, Civil Action No. 07-CV-5367 (FLW) (TJB), *Celgene Corporation, Novartis Pharmaceuticals Corporation and Novartis Pharma A.G. v. Actavis South Atlantic LLC and Abrika Pharmaceuticals, Inc.*: Answer and Counterclaims, Dec. 18, 2007.

In the United District Court For The District of New Jersey, Civil Action No. 07-CV-5367 (FLW) (TJB), *Celgene Corporation, Novartis Pharmaceuticals Corporation and Novartis Pharma A.G. v. Actavis South Atlantic LLC and Abrika Pharmaceuticals, Inc.*: Plaintiffs' Reply to Defendants' Answer and Counterclaims, Jan. 25, 2008.

In the United District Court For The District of New Jersey, Civil Action No. 07-CV-5552 (SDW) (MCA), *Celgene Corporation, Novartis Pharmaceuticals Corporation and Novartis Pharma A.G. v. Barr Pharmaccuticals, Inc. and Barr Laboratories, Inc.*: Complaint for Patent Infringement, Nov. 16, 2007.

In the United District Court For The District of New Jersey, Civil Action No. 07-CV-5367 (FLW) (TJB), *Celgene Corporation, Novartis Pharmaceuticals Corporation and Novartis Pharma A.G. v. Actavis South Atlantic LLC and Abrika Pharmaceuticals, Inc.*: Defendants' Answer, Affirmative Defenses, Counterclaims and Jury Demand, Jan. 25, 2008.

In the United District Court For The District of New Jersey, Civil Action No. 07-CV-5367 (FLW) (TJB), *Celgene Corporation, Novartis Pharmaceuticals Corporation and Novartis Pharma A.G. v. Actavis South Atlantic LLC and Abrika Pharmaceuticals, Inc.*: Plaintiff's Reply to Defendants' Counterclaims, Mar. 5, 2008.

* cited by examiner

PROCESSES AND INTERMEDIATES FOR RESOLVING PIPERIDYL ACETAMIDE STEREOISOMERS

This application is a continuation of U.S. application Ser. No. 10/915,905; filed Aug. 11, 2004 now abandoned which is a continuation of U.S. application Ser. No. 09/283,645, filed Apr. 1, 1999, now U.S. Pat. No. 6,962,997 the contents of which are incorporated herein by reference, which is a continuation of U.S. Pat. No. 5,936,091, issued Aug. 10, 1999 from U.S. patent application Ser. No. 08/861,988 filed May 22, 1997, which is also incorporated herein by reference.

FIELD OF THE INVENTION

This invention is directed to novel processes for resolution of piperidyl acetamide stereoisomers. The invention additionally is directed to synthetic intermediates and reaction products useful in such processes.

BACKGROUND OF THE INVENTION

Substituted piperidines have found use in the treatment of many nervous system disorders. For example, methylphenidate has been used to treat Attention Deficit Disorder (ADD), Attention Deficit Hyperactivity Disorder (ADHD) and cognitive decline in Acquired Immunodeficiency Syndrome (AIDS) and AIDS Related Complex (ARC) patients. (See, e.g., Greenhill, *Child & Adol. Psych. Clin. N.A.,* 1995, 4, 123, and Brown, *Intl. J. Psychl. Med,* 1995, 25, 21).

Many currently available synthetic routes to methylphenidate and other substituted piperidines involve preparation of racemic mixtures. (See, e.g., U.S. Pat. No. 2,507,631, to Hartmann, et al., and U.S. Pat. No. 2,957,880, to Rometsch, et al.). There are, however, a number of disadvantages associated with racemic mixtures of such drugs. Current administration of racemic methylphenidate often results in notable side effects such as anorexia, weight loss, insomnia, dizziness and dysphoria. Additionally, racemic methylphenidate produces a euphoric effect when administered intravenously or through inhalation, and thus carries a high potential for substance abuse in patients.

U.S. Pat. Nos. 2,507,631 and 2,957,880 disclose synthetic procedures wherein methylphenidate, alternatively known as methyl α-piperid-2-ylphenylacetate, is prepared through a multi-step process in which 2-chloropyridine and phenylacetonitrile initially are coupled to form α-pyrid-2-ylphenylacetonitrile. The resulting α-pyrid-2-ylphenylacetonitrile then is hydrated in the presence of acid to yield α-pyrid-2-ylphenylacetamide which, in turn, is either: (a) catalytically hydrogenated to yield α-piperid-2-ylphenylacetamide and then converted to methyl α-piperid-2-ylphenylacetate, or (b) converted to methyl α-pyrid-2-ylphenylacetate which, in turn, is hydrogenated to yield methyl α-piperid-2-ylphenylacetate.

In the first embodiment of U.S. Pat. No. 2,507,631 and in the process described in U.S. Pat. No. 2,957,880, α-piperid-2-ylphenylacetamide is first separated into the threo and erythro diastereomeric racemates. This is accomplished through evaporation of the solvent utilized in the hydrogenation (i.e., acetic acid), addition of sodium hydroxide to precipitate the α-piperid-2-ylphenylacetamide free base, recrystallization of this amide from ethyl acetate, and preferential crystallization of the erythro form by passing gaseous hydrogen chloride through an ethanolic solution of the amide.

The isolated erythro racemate then is resolved through formation of the l-tartrate salt, repeated recrystallizations of this salt from 96% ethanol are performed until a constant rotation is obtained, and the l-erythro form of α-piperid-2-ylphenylacetamide is precipitated with sodium hydroxide. The l-erythro form of α-piperid-2-ylphenylacetamide thus obtained is said to be subjected to epimerization to yield the desired d-threo diastereomer of α-piperid-2-ylphenylacetamide through treatment with 6 M potassium hydroxide. According to the disclosed procedure, the α-piperid-2-ylphenylacetamide thus obtained is converted to d-threo methyl α-piperid-2-ylphenylacetate through hydrolysis and esterification.

Some in the art have raised doubts as to whether the procedures disclosed in U.S. Pat. Nos. 2,507,631 and 2,957,880 do, in fact, produce the desired d-threo isomer. Indeed, J. R. Soares, "Stereochemical Studies On Potential Central Nervous System Active Agents and Studies On The Chemistry Of Some 3-Benzoylpiperidines," 1971, Columbia University Ph.D. dissertation, p. 115, discloses that "all attempts to epimerize the resolved erythro-amides to the corresponding threo-amides by the procedure outlined in [U.S. Pat. No. 2,957,880] failed completely."

In any event, the synthetic procedure described in U.S. Pat. Nos. 2,507,631 and 2,957,880 is wasteful in that it involves discarding the threo α-piperid-2-ylphenylacetamide racemate which is isolated following the recrystallization step and which typically represents approximately 25% of the acetamide product obtained via hydrogenation.

Consequently, there remains a need in the art for alternative synthetic procedures for the preparation of methylphenidate and other substituted piperidines. In particular, there is a need for synthetic procedures that do not require separating and discarding threo stereoisomers from the hydrogenation reaction product.

OBJECTS OF THE INVENTION

It is an object of the present invention to provide processes for the preparation of substituted piperidines.

It is another object of this invention to provide processes that provide synthetic intermediates and, hence, products having high optical purity.

It is yet another object to provide processes that proceed more efficiently than the processes disclosed by the prior art.

SUMMARY OF THE INVENTION

These and other objects are satisfied by the present invention, which provides processes and intermediates for preparing piperidyl acetamides. In preferred embodiments, the processes of the invention comprise reacting d,l-threo piperidyl acetamide stereoisomers having formulas IIa and IIb:

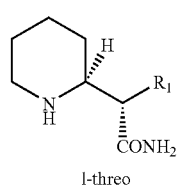

IIa l-threo

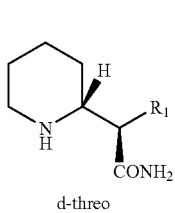

d-threo (R₁=aryl having about 6 to about 28 carbon atoms) with an acid resolving agent in an organic solvent, thereby forming acid salts of the d-threo stereoisomers preferentially with respect to the l-threo stereoisomers. The resulting acid salts then are reacted with aqueous base to form the corresponding piperidyl acetamide, which subsequently is converted to a corresponding ester.

DETAILED DESCRIPTION OF THE INVENTION

This invention provides novel processes for stereoselective synthesis of a variety 2-substituted piperidine stereoisomers. In one aspect, the invention is directed to synthetic methods involving hydrogenation of pyridines having formula I:

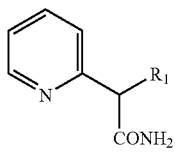

wherein $R_1$ is aryl having about 6 to about 28 carbon atoms. Aryl groups, as used herein, are aromatic groups containing a delocalized π-electron cloud. Such aromatic groups can be substituted with one or more substituents, such as, for example, halo, alkyl, aryl, hydroxy, alkoxy, carboxy, and cycloalkyl. Exemplary aryl groups include phenyl, naphthyl, xylyl, chlorophenyl, fluorophenyl, trifluoromethylphenyl, and bromophenyl. Phenyl groups are preferred.

This hydrogenation can be effected by any of the numerous techniques known in the art. One preferred hydrogenation technique involves reacting the pyridine with hydrogen gas in the presence of a suitable catalyst in an alkanoic acid having 1 to about 10 carbon atoms. The hydrogenation preferably run at 25° C. and 40 psi. Representative catalysts contain platinum, with platinum oxide being particularly preferred. One preferred alkanoic acid is acetic acid.

Hydrogenation of pyridine I provides a mixture of piperidine diastereomers IIa-d:

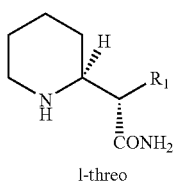

l-threo

d-erythro

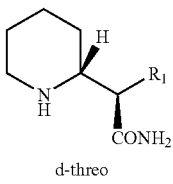

d-threo

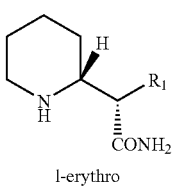

l-erythro

In accordance with the present invention, this mixture is treated with an organic base in an organic solvent to epimerize the erythro stereoisomers into threo forms. The epimerization can, for example, be effected in an aromatic hydrocarbon solvent such as toluene using an alkali metal alkoxide such as potassium tert-butoxide. In preferred embodiments, the epimerization is effected at 70° C. in an aromatic hydrocarbon solvent such as toluene using two equivalents of an alkali metal alkoxide such as potassium tert-butoxide.

The resulting composition, which should consist predominantly of d,l-threo piperidyl acetamide stereoisomers, is reacted with an acid resolving agent in an organic solvent, thereby forming acid salts of the d-threo stereoisomers preferentially with respect to the l-threo stereoisomers. Alkyl groups according to the invention are hydrocarbons which are straight, branched, or cyclic. Such hydrocarbons can be substituted with one or more substituents, such as, for example, halo, hydroxy, alkoxy, and carboxy groups. Exemplary alkyl groups include methyl, ethyl, isopropyl, n-butyl, t-butyl, n-pentyl, acetyl, trifluoromethyl, chloromethyl, and hexyl groups. Representative solvents include alcohols, alkyl alkanoates (e.g., ethyl acetate), ketones (e.g., acetone), and ethers (e.g., tetrahydrofuran, dioxane). Preferred solvents are alcohols having 1 to about 5 carbon atoms, include branched and straight chain compounds such as ethyl, propyl and tert-butyl alcohol, with isopropanol being particularly preferred. The reaction of piperidyl acetamide stereoisomers with acid resolving agents preferably is performed with stirring at room temperature.

Representative acid resolving agents include L-(+)- or D-(−)-tartaric acid, dipivaloyl-D-tartaric acid, (1S)-(+)-10-camphorsulphonic acid, L-(−)-malic acid, (S)-(+)-mandelic acid, N-acetyl-l-aspartic acid (and other N-protected amino acids), (R)-(+)-1,1'-bi-s-napthol, (+)-camphoric acid, D-glucuronic acid, and derivatives thereof. Those believed to be useful for forming d-threo stereoisomers preferentially with respect to l-threo isomers include (+)-dibenzoyl-D-tartaric acid. Derivatives of D-(−)-tartaric acid are preferred, including those having formula (III):

$$HO_2CCH[OC(O)R_3]CH[OC(O)R_3]CO_2H \qquad (III)$$

where each $R_3$, independently, is aryl having 6 to about 28 carbon atoms or aralkyl having 7 to about 28 carbon atoms. Aralkyl groups according to the invention are those (such as, for example, benzyl groups, which both aryl and alkyl portions and are covalently bound to a core molecule (such as the above-noted carbonyl-functionalized tartaric acid) through the alkyl portions thereof.

In certain alternative embodiments of the invention, the piperidyl acetamide stereoisomers having formulas IIa and IIb are reacted with an acid resolving agent in an organic solvent to form acid salts of the l-threo stereoisomers preferentially with respect to the d-threo stereoisomers. Resolving agents believed to be useful for forming l-threo stereoisomers preferentially with respect to d-threo isomers include (−)-dibenzoyl-L-tartaric acid. Derivatives of L-(−)-tartaric acid are preferred, including those having formula (III). Crystallization preferably is performed at ambient temperature.

The acid salts obtained via resolution typically are dissolved in water and treated with an aqueous base such as a carbonate, bicarbonate, or hydroxide to precipitate the corresponding piperidyl amide free base in substantially pure form. They then can be reacted with an alcohol having, for example, 1 to about 5 carbon atoms in the presence of acid to form the corresponding ester.

Additional objects, advantages, and novel features of this invention will become apparent to those skilled in the art upon examination of the following examples thereof, which are not intended to be limiting.

EXAMPLE 1

Preparation of d-Threo-methylphenidate Hydrochloride Via Diastereomeric Separation and Resolution of d,l-erythro-Amide (Comparative Example)

A. α-Phenyl-α-pyridyl-(2)-acetonitrile

Materials:

| 2-Chloropyridine (99%) | 286 g (2.50 moles) |
| Benzyl cyanide (98%) | 314 g (2.62 moles) |
| Sodium amide (90%) | 217 g (5.00 moles) |
| Toluene | 0.98 + 0.17 L |
| Water | 0.87 L |
| Ethyl acetate | 0.43 L |
| Hexanes | 1.56 + 1.95 L |
| Brine | 0.43 L |

Procedure:

A 5L multi-neck glass reactor was charged with 2-chloropyridine. benzyl cyanide, and toluene (0.98 L). Sodium amide powder was added over a 1 h period via a solid-addition funnel, keeping the reaction temperature below 30° C. The reaction mixture was stirred for 16 h at ambient temperature. The reaction was then cooled to ~10° C., and quenched with 0.87 L water. Ethyl acetate (0.43 L) was added to solubilize the precipitated product. The organic layer was separated and washed once with 0.43 L brine. Solvent was removed from the organic layer on a rotovap, and toluene (0.17 L), followed by hexanes (1.56 L), were added to the resulting residue. The resulting slurry was filtered. The filter cake was washed with hexanes (1.95 L), and dried to give 441 g of α-phenyl-α-pyridyl-(2)-acetonitrile as light brown crystals (90% yield based on 2-chloropyridine).

B. α-Phenyl-α-pyridyl-(2)-acetamide

Materials:

| α-Phenyl-α-pyridyl-(2)-acetonitrile | 441 g (2.27 moles) |
| Conc. $H_2SO_4$ | 0.55 L |
| Water | 1.63 L |
| 50% NaOH | 1.27 L |

Procedure:

The reactor was charged with conc. $H_2SO_4$, and cooled to ~10° C. α-Phenyl-α-pyridyl-(2)-acetonitrile (from Example 1.A) was added portionwise, keeping the temperature below 30° C. The reaction was stirred at ambient temperature for 16 h. The reaction mixture then was cooled to 10° C., at which point water was added. The NaOH then was added to a pH of 12, keeping the temperature below 30° C. The resulting crystals were filtered, and the filter cake was washed with water and dried under vacuum to give 482 g (100%) of α-phenyl-α-pyridyl-(2)-acetamide.

$NH_4OH$ can be substituted for NaOH to adjust the pH to 12. One advantage of using $NH_4OH$ is that the by-product that is formed (ammonium sulfate) is more soluble in water then the by-product (sodium sulfate) formed when NaOH is used as the base. Thus, the product crystals are less likely to be contaminated with inorganic salts.

C. d,l-erythro-α-Phenyl-α-piperidyl-(2)-acetamide

Materials:

| α-Phenyl-α-pyridyl-(2)-acetamide | 482 g (2.27 moles) |
| Platinum oxide ($PtO_2$) | 8.06 g |
| Acetic acid | 1.68 + 4.13 L |
| Celite | 500 + 250 g |
| Ethyl acetate | 3.10 + 0.62 + 2.07 + 2.07 + 4.13 + 0.21 L |
| Water | 4.13 + 1.03 + 2.07 L |
| 50% NaOH | 0.56 L |

Procedure:

The reactor was charged with α-phenyl-α-pyridyl-(2)-acetamide (from Example 1.B), acetic acid (1.68 L), and $PtO_2$. The reactor then was filled with hydrogen gas, and pressurized to 60 psi. The reaction mixture was hydrogenated at room temperature for 16 h. The reaction mixture was filtered through a pad of Celite (500 g) to remove catalyst, and the Celite pad washed with acetic acid (4.13 L). The filtrate was concentrated under reduced pressure. Ethyl acetate (3.10 L) was added to the residue and stirred for 2h. The resulting crystals (first crop) were filtered, washed with ethyl acetate (0.62 L), and dried. The filtrate was concentrated under reduced pressure. Ethyl acetate (2.07 L) was added to the residue and stirred for 2 h. The resulting crystals (second crop) were filtered, washed with ethyl acetate (2.07 L), and dried. The crystals from first and second crops were combined and dissolved in water (4.13 L), filtered through a pad of Celite (250 g), and the Celite pad was washed with water (1.03 L). The resulting filtrate was cooled to 10° C., followed by addition of 50% NaOH until the pH of the mixture was 13 and the free amine crystallized out. The crystals were filtered, washed with water (2.07 L). and dried to give 297 g (60%) of d,l-erythro-α-phenyl-α-piperidyl-(2)-acetamide.

D. l-erythro-α-Phenyl-α-piperidyl-(2)-acetamide

Materials:

| | |
|---|---|
| d,l-erythro-α-phenyl-α-piperidyl-(2)-acetamide | 297.2 g (1.361 moles) |
| D-(−)-Tartaric acid | 204.3 g (1.361 moles) |
| Methanol | 7.13 + 7.13 L |
| Water | 2.0 L |
| 50% NaOH | 0.1 L |

Procedure:

D-(−)-Tartaric acid dissolved in methanol (7.13 L) was added to a stirred solution of d,l-erythro-α-phenyl-d-piperidyl-(2)-acetamide (from Example 1.C), dissolved in methanol (7.13 L). The resulting clear solution was stirred for 16 h, whereby the tartrate salt of l-erythro-acetamide crystallized out. The crystals were filtered, washed with methanol and dried. This tartrate salt was dissolved in water and 50% NaOH was added to a pH of 12, whereby the free base precipitated out. The precipitated crystals were filtered, washed with water and dried to give 119 g (40%) of l-erythro-α-phenyl-α-piperidyl-(2)-acetamide.

E. d-threo-α-Phenyl-α-piperidyl-(2)-acetamide

Materials:

| | |
|---|---|
| l-erythro-α-phenyl-α-piperidyl-(2)-acetamide | 119 g (0.544 moles) |
| Potassium t-butoxide (95%) | 141.5 g (1.198 moles) |
| Toluene | 3.57 L |
| Water | 0.60 + 0.30 + 1.20 L |
| Conc. HCl | 0..24 + 0.12 L |
| 50% NaOH | 0.14 L |

Procedure:

A mixture of l-erythro-α-phenyl-α-piperidyl-(2)-acetamide (from Example 1.D), potassium t-butoxide, and toluene was heated to 70° C. and stirred for 16 h. The reaction mixture was cooled to room temperature, followed by slow addition of water (0.60 L). Conc. HCl (0.24 L) was added to this resulting mixture, and stirred for 0.5 h. The layers were separated, and the top organic layer was washed with a prepared solution of conc. HCl (0.12 L) and water (0.30 L). The combined aqueous layers were cooled to 10° C., and 50% NaOH was added to a pH of 12, whereby the free base precipitated out. The crystals were filtered, washed with water (1.20 L), and dried to give 101 g (85%) of d-threo-α-phenyl-α-piperidyl-(2)-acetamide.

F. d-threo-Methylphenidate Hydrochloride

Materials:

| | |
|---|---|
| d-threo-α-phenyl-α-piperidyl-(2)-acetamide | 101 g (0.46 moles) |
| Conc. $H_2SO_4$ | 121 mL |
| Methanol | 1.1 L |
| Water | 0.81 L |
| 50% NaOH | 175 mL |
| Diethyl ether | 1.0 + 1.0 + 1.0 + 1.0 L |
| Magnesium sulfate | 20 g |
| HCl gas | As needed. |

Procedure:

A solution of d-threo-α-phenyl-α-piperidyl-(2)-acetamide (from Example 1.E) and conc. $H_2SO_4$ in methanol was heated to reflux and stirred for 2 days. The reaction mixture was cooled to room temperature and concentrated under reduced pressure. Water (0.81 L) and ether (1.0 L) were added to the residue. NaOH was added to a pH of 12, and the layers were separated. The aqueous layer was extracted with ether (1.0 L). $MgSO_4$ was added to the combined ether layers, filtered, and washed with ether (1.0 L). HCl gas was passed through the filtrate with stirring, whereby white crystals of d-threo-methylphenidate hydrochloride precipitated out. The crystals were filtered, washed with ether (1.0 L), and dried to give 100 g (80%) of d-threo-methylphenidate hydrochloride.

The overall yield for Example 1 was 14.7%.

EXAMPLE 2

Preparation of d-Threo-methylphenidate Hydrochloride Via Epimerization and Resolution of d,l-Threo-amide Enantiomers

A. α-Phenyl-α-pyridyl-2-acetonitrile

Materials:

| | |
|---|---|
| 2-Chloropyridine (99%) | 172 g (1.50 moles) |
| Benzyl cyanide (98%) | 188 g (1.576 moles) |
| Sodium amide (90%) | 130 g (3.00 moles) |
| Toluene | 0.59 + 0.10 L |
| Water | 0.52 L |
| Ethyl acetate | 0.26 L |
| Hexanes | 0.94 + 1.17 L |
| Brine | 0.26 L |

Procedure:

The reactor was charged with 2-chloropyridine, benzyl cyanide, and toluene (0.59 L). Sodium amide powder was added over a 1 h period via a solid-addition funnel, keeping the reaction temperature below 300° C. The reaction mixture was stirred for 16 h at ambient temperature. The reaction was cooled to ~10° C., and quenched with 0.52 L water. Ethyl acetate (0.26 L) was added to solubilize the precipitated product. The organic layer was separated and washed once with 0.26 L brine, and solvent was removed from the organic layer on a rotovap. Toluene (0.10 L), followed by hexanes (0.94 L) were added to the resulting residue. The resulting slurry was filtered, and the filter cake was washed with hexanes (1.17 L), and dried to give 265 g of α-phenyl-α-pyridyl-(2)-acetonitrile as light brown crystals (90% yield based on 2-chloropyridine).

B. α-Phenyl-α-pyridyl-(2)-acetamide

Materials:

| | |
|---|---|
| α-Phenyl-α-pyridyl-(2)-acetonitrile | 264 g (1.362 moles) |
| Conc. H$_2$SO$_4$ | 0.33 L (6.226 moles) |
| Water | 0.98 L |
| 50% NaOH | 0.77 L |

Procedure:

The reactor was charged with conc. H$_2$SO$_4$, and cooled to ~10° C. α-Phenyl-α-pyridyl-(2)-acetonitrile (from Example 2.A) was added portionwise, keeping the temperature below 30° C. The reaction was stirred at ambient temperature for 16 h. The reaction mixture then was cooled to 10° C., the water was added, and the NaOH was added to a pH of 12, keeping the temperature below 30° C. The resulting crystals were filtered, the filter cake was washed with water, and dried under vacuum to give 289 g (100%) of α-phenyl-α-pyridyl-(2)-acetamide.

C. d,l-erythro/threo-α-Phenyl-α-piperidyl-(2)-acetamide

Materials:

| | |
|---|---|
| α-Phenyl-α-pyridyl-(2)-acetamide | 289 g (1.365 moles) |
| Platinum oxide (PtO$_2$) | 4.84 g |
| Acetic acid | 1.01 + 2.48 L |
| Celite | 300 + 150 g |
| Water | 2.48 + 0.62 + 1.24 L |
| 50% NaOH | 0.33 L |

Procedure:

The reactor was charged with α-phenyl-α-pyridyl-(2)-acetamide (from Example 2.B), acetic acid (1.01 L), and PtO$_2$. The reactor then was filled with hydrogen gas, pressurized to 60 psi, and the mixture hydrogenated at room temperature for 16 h. The reaction mixture then was filtered through a pad of Celite (300 g) to remove the catalyst, and the Celite pad is washed with acetic acid (2.48 L). The filtrate was concentrated under reduced pressure. The resulting residue was dissolved in water (2.48 L), filtered through a pad of Celite (150 g), and the Celite pad was washed with water (0.62 L). The resulting filtrate was cooled to 10° C., followed by addition of 50% NaOH until the pH of the mixture was 13 and the free amine crystallized out. The crystals were filtered, washed with water (1.24 L), and dried to give 297 g (100%) of a 4:1 mixture of d,l-erythro-α-phenyl-α-piperidyl-(2)-acetamide and d,l-threo-α-phenyl-α-piperidyl-(2)-acetamide.

D. d,l-threo-α-Phenyl-α-piperidyl-(2)-acetamide

Materials:

| | |
|---|---|
| Mixture of d,l-erythro-acetamide and d,l-threo-acetamide | 297 g (1.36 moles) |
| Potassium t-butoxide (95%) | 354 g (2.996 moles) |
| Toluene | 8.92 L |
| Water | 1.49 + 0.74 + 3.00 L |
| Conc. HCl | 0.59 + 0.30 L |
| 50% NaOH | 0.36 L |

Procedure:

A mixture of d,l-erythro-acetamide and d,l-threo-acetamide (from Example 2.C), potassium t-butoxide, and toluene was heated to 70° C. and stirred for 16 h. The reaction mixture was cooled to room temperature, followed by slow addition of water (1.49 L). Conc. HCl (0.59 L) was added to this resulting mixture, which was stirred for 0.5 h. The layers were separated, and the top organic layer was then washed with a prepared solution of conc. HCl (0.30 L) and water (0.74 L). The combined aqueous layers were cooled to 10° C., and 50% NaOH was added to a pH of 12 whereby the free base precipitated out. The crystals were filtered, washed with water (3.00 L), and dried to give 253 g (85%) of d,l-threo-α-phenyl-α-piperidyl-(2)-acetamide.

E. d-threo-α-Phenyl-α-piperidyl-(2)-acetamide

Materials:

| | |
|---|---|
| d,l-threo-α-phenyl-α-piperidyl-(2)-acetamide | 253 g (1.159 moles) |
| Dibenzoyl-D-tartaric acid | 415 g (1.159 moles) |
| Isopropanol | 8.11 L |
| 6N HCl (aqueous) | 1.67 L |
| Water | 1.0 L |
| Solid NaCl | 290 g |
| 50% NaOH (aqueous) | 1.0 L |

Procedure:

Dibenzoyl-D-tartaric acid and d,l-threo-α-phenyl-α-piperidyl-(2)-acetamide (from Example 2.D) were dissolved in isopropanol by warming the reaction mixture to ~50° C. The resulting clear solution was stirred at ambient temperature for 16 h, whereby the tartrate salt of d-threo-acetamide crystallized out. The crystals were filtered, and the filter cake was washed with isopropanol and dried in a vacuum oven at 40° C. This tartrate salt was added in portions to a stirred solution of 6N aq. HCl, and the resultant slurry was stirred at ambient temperature for 4 h. The slurry was filtered, and the filter cake (containing free dibenzoyl-D-tartaric acid) was washed with water. Solid NaCl was added to the filtrate (which contained d-threo-acetamide hydrochloride salt) and the mixture was cooled to ~10° C. The NaOH was added to this mixture to a pH of 12, whereby the free base of d-threo-acetamide precipitated out. The precipitated crystals were filtered, washed with water and dried to give 101 g (40%) of d-threo-α-phenyl-α-piperidyl-(2)-acetamide.

F. d-threo-Methylphenidate Hydrochloride

Materials:

| | |
|---|---|
| d-threo-α-phenyl-α-piperidyl-(2)-acetamide | 101 g (0.46 moles) |
| Conc. H$_2$SO$_4$ | 121 mL |
| Methanol | 1.1 L |
| Water | 0.81 L |

-continued

| 50% NaOH | 175 mL |
| Diethyl ether | 1.0 + 1.0 + 1.0 + 1.0 L |
| Magnesium sulfate | 20 g |
| HCl gas | As needed. |

Procedure:

A solution of d-threo-α-phenyl-α-piperidyl-(2)-acetamide (from Example 2.E) and conc. $H_2SO_4$ in methanol was heated to reflux and stirred for 2 days. The reaction mixture was cooled to room temperature and concentrated under reduced pressure. Water (0.81 L) and ether (1.0 L) were added to the residue. The NaOH was added to a pH of 12, and the layers were separated. The aqueous layer was extracted with ether (1.0 L). $MgSO_4$ was added to the combined ether layers, filtered, and washed with ether (1.0 L). HCl gas was passed through the filtrate with stirring, whereby white crystals of d-threo-methylphenidate hydrochloride precipitated out. The crystals were filtered, washed with ether (1.0 L), and dried to give 100 g (80%) of d-threo-methylphenidate hydrochloride.

In contrast to Example 1, the overall yield for Example 2 was 24.5%, an increase of over 66%.

EXAMPLE 3

Preparation of l-Threo-methylphenidate Hydrochloride Via Epimerization and Resolution of d,l-Threo-amide Enantiomers A. α-Phenyl-α-pyridyl-2-acetonitrile Materials:

| 2-Chloropyridine (99%) | 172 g (1.50 moles) |
| Benzyl cyanide (98%) | 188 g (1.576 moles) |
| Sodium amide (90%) | 130 g (3.00 moles) |
| Toluene | 0.59 + 0.10 L |
| Water | 0.52 L |
| Ethyl acetate | 0.26 L |
| Hexanes | 0.94 + 1.17 L |
| Brine | 0.26 L |

Procedure:

The reactor was charged with 2-chloropyridine, benzyl cyanide, and toluene (0.59 L). Sodium amide powder was added over a 1 h period via a solid-addition funnel, keeping the reaction temperature below 300° C. The reaction mixture was stirred for 16 h at ambient temperature. The reaction was cooled to ~10° C., and quenched with 0.52 L water. Ethyl acetate (0.26 L) was added to solubilize the precipitated product. The organic layer was separated and washed once with 0.26 L brine, and solvent was removed from the organic layer on a rotovap. Toluene (0.10 L), followed by hexanes (0.94 L) were added to the resulting residue. The resulting slurry was filtered, and the filter cake was washed with hexanes (1.17 L), and dried to give 265 g of α-phenyl-α-pyridyl-(2)-acetonitrile as light brown crystals (90% yield based on 2-chloropyridine).

B. α-Phenyl-α-pyridyl-(2)-acetamide

Materials:

| α-Phenyl-α-pyridyl-(2)-acetonitrile | 264 g (1.362 moles) |
| Conc. $H_2SO_4$ | 0.33 L (6.226 moles) |
| Water | 0.98 L |
| 50% NaOH | 0.77 L |

Procedure:

The reactor was charged with conc. $H_2SO_4$, and cooled to ~10° C. α-Phenyl-α-pyridyl-(2)-acetonitrile (from Example 3.A) was added portionwise, keeping the temperature below 30° C. The reaction was stirred at ambient temperature for 16 h. The reaction mixture then was cooled to 10° C., the water was added, and the NaOH was added to a pH of 12, keeping the temperature below 30° C. The resulting crystals were filtered, the filter cake was washed with water, and dried under vacuum to give 289 g (100%) of α-phenyl-α-pyridyl-(2)-acetamide.

C. d,l-erythro/threo-α-Phenyl-α-piperidyl-(2)-acetamide

Materials:

| α-Phenyl-α-pyridyl-(2)-acetamide | 289 g (1.365 moles) |
| Platinum oxide ($PtO_2$) | 4.84 g |
| Acetic acid | 1.01 + 2.48 L |
| Celite | 300 + 150 g |
| Water | 2.48 + 0.62 + 1.24 L |
| 50% NaOH | 0.33 L |

Procedure:

The reactor was charged with α-phenyl-α-pyridyl-(2)-acetamide (from Example 3.B), acetic acid (1.01 L), and $PtO_2$. The reactor then was filled with hydrogen gas, pressurized to 60 psi, and the mixture hydrogenated at room temperature for 16 h. The reaction mixture then was filtered through a pad of Celite (300 g) to remove the catalyst, and the Celite pad is washed with acetic acid (2.48 L). The filtrate was concentrated under reduced pressure. The resulting residue was dissolved in water (2.48 L), filtered through a pad of Celite (150 g), and the Celite pad was washed with water (0.62 L). The resulting filtrate was cooled to 10° C., followed by addition of 50% NaOH until the pH of the mixture was 13 and the free amine crystallized out. The crystals were filtered, washed with water (1.24 L), and dried to give 297 g (100%) of a 4:1 mixture of d,l-erythro-α-phenyl-α-piperidyl-(2)-acetamide and d,l-threo-α-phenyl-α-piperidyl-(2)-acetamide.

D. d,l-threo-α-Phenyl-α-piperidyl-(2)-acetamide

Materials:

| Mixture of d,l-erythro-acetamide and d,l-threo-acetamide | 297 g (1.36 moles) |
| Potassium t-butoxide (95%) | 354 g (2.996 moles) |
| Toluene | 8.92 L |
| Water | 1.49 + 0.74 + 3.00 L |
| Conc. HCl | 0.59 + 0.30 L |
| 50% NaOH | 0.36 L |

Procedure:

A mixture of d,l-erythro-acetamide and d,l-threo-acetamide (from Example 3.C), potassium t-butoxide, and toluene was heated to 70° C. and stirred for 16 h. The reaction mixture was cooled to room temperature, followed by slow addition of water (1.49 L). Conc. HCl (0.59 L) was added to this resulting mixture, which was stirred for 0.5 h. The layers were separated, and the top organic layer was then washed with a prepared solution of conc. HCl (0.30 L) and water (0.74 L). The combined aqueous layers were cooled to 10° C., and 50% NaOH was added to a pH of 12 whereby the free base precipitated out. The crystals were filtered, washed with water (3.00 L), and dried to give 253 g (85%) of d,l-threo-α-phenyl-α-piperidyl-(2)-acetamide.

E. 1-threo-α-Phenyl-α-piperidyl-(2)-acetamide

Materials:

| | |
|---|---|
| d,l-threo-α-phenyl-α-piperidyl-(2)-acetamide | 253 g (1.159 moles) |
| Dibenzoyl-L-tartaric acid | 415 g (1.159 moles) |
| Isopropanol | 8.11 L |
| 6N HCl (aqueous) | 1.67 L |
| Water | 1.0 L |
| Solid NaCl | 290 g |
| 50% NaOH (aqueous) | 1.0 L |

Procedure:

Dibenzoyl-L-tartaric acid and d,l-threo-α-phenyl-α-piperidyl-(2)-acetamide (from Example 3.D) is dissolved in isopropanol by warming the reaction mixture to ~50° C. The resulting clear solution is stirred at ambient temperature for 16 h, whereby the tartrate salt of l-threo-acetamide crystallizes out. The crystals are filtered, and the filter cake washed with isopropanol and dried in a vacuum oven at 40° C. This tartrate salt is added in portions to a stirred solution of 6N aq. HCl, and the resultant slurry is stirred at ambient temperature for 4 h. The slurry is filtered, and the filter cake (containing free dibenzoyl-L-tartaric acid) is washed with water. Solid NaCl is added to the filtrate (which contains l-threo-acetamide hydrochloride salt) and the mixture is cooled to ~10° C. The NaOH is added to this mixture to a pH of 12, whereby the free base of l-threo-acetamide precipitates out. The precipitated crystals are filtered, washed with water and dried to give l-threo-α-phenyl-α-piperidyl-(2)- acetamide.

F. l-threo-Methylphenidate Hydrochloride

Materials:

| | |
|---|---|
| l-threo-α-phenyl-α-piperidyl-(2)-acetamide | 101 g (0.46 moles) |
| Conc. H$_2$SO$_4$ | 121 mL |
| Methanol | 1.1 L |
| Water | 0.81 L |
| 50% NaOH | 175 mL |
| Diethyl ether | 1.0 + 1.0 + 1.0 + 1.0 L |
| Magnesium sulfate | 20 g |
| HCl gas | As needed. |

Procedure:

A solution of l-threo-α-phenyl-α-piperidyl-(2)- acetamide (from Example 3.E) and conc. H$_2$SO$_4$ in methanol is heated to reflux and stirred for 2 days. The reaction mixture is cooled to room temperature and concentrated under reduced pressure. Water (0.81 L) and ether (1.0 L) are added to the residue. The NaOH is added to a pH of 12, and the layers are separated. The aqueous layer is extracted with ether (1.0 L). MgSO$_4$ is added to the combined ether layers, filtered, and washed with ether (1.0 L). HCl gas is passed through the filtrate with stirring, whereby white crystals of l-threo--methylphenidate hydrochloride precipitate out. The crystals are filtered, washed with ether (1.0 L), and dried to give l-threo-methylphenidate hydrochloride.

Those skilled in the art will appreciate that numerous changes and modifications may be made to the preferred embodiments of the present invention and that such changes and modifications may be made without departing from the spirit of the invention. It is therefore intended that the appended claims cover all such equivalent variations as fall within the true spirit and scope of the invention.

What is claimed is:

1. A synthetic process comprising the steps of:
providing a mixture of said d,l-threo piperidyl acetamide stereoisomers having formulas:

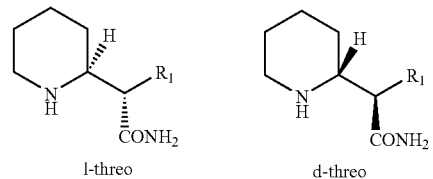

l-threo          d-threo wherein $R_1$ is aryl having about 6 to about 28 carbon atoms;
reacting said stereoisomers with an acid resolving agent having the formula

HO$_2$CCH[OC(O)R$_3$]CH[OC(O)R$_3$]CO$_2$H wherein each $R_3$ is phenyl in an organic solvent comprising an alcohol, an alkyl alkanoate, a ketone, or an ether, and thereby forming acid salts; and
physically isolating said acid salts.

2. The process of claim 1 wherein $R_1$ is phenyl.

3. The process of claim 1 wherein said solvent is an alkyl alcohol having 1 to about 5 carbon atoms.

4. The process of claim 3 wherein said alkyl alcohol is isopropanol.

5. The process of claim 1, wherein said physically isolated acid salts are d-threo acid salts, said process further comprising reacting said d-threo acid salts with aqueous base to form said d-threo piperidine acetamide.

6. The process of claim 5 further comprising reacting said d-threo piperidine acetamide with an alcohol having 1 to about 5 carbon atoms in the presence of acid to form a d-threo piperidine acetate.

7. The process of claim 1 wherein said d,l-threo piperidyl acetamide stereoisomers are prepared by reacting a pyridine having formula:

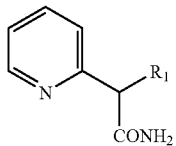

with hydrogen in an alkanoic acid having 1 to about 10 carbon atoms in the presence of a catalyst to provide a mixture of threo and erythro piperidyl stereoisomers; and contacting said erythro stereoisomers with organic base, thereby converting said erythro piperidyl stereoisomers to threo piperidyl stereoisomers.

8. The product of the process of claim 1.

* * * * *